United States Patent
Galstian et al.

(10) Patent No.: US 10,631,715 B2
(45) Date of Patent: Apr. 28, 2020

(54) TUNABLE OPTICAL DEVICE, TUNABLE LIQUID CRYSTAL LENS ASSEMBLY AND IMAGING SYSTEM USING SAME

(71) Applicant: UNIVERSITÉ LAVAL, Québec (CA)

(72) Inventors: Tigran Galstian, Quebec (CA); Armen Saghatelyan, Quebec (CA); Arutyun Bagramyan, Quebec (CA)

(73) Assignee: UNIVERSITÉ LAVAL, Quebec (CA)

( * ) Notice: Subject to any disclaimer, the term of this patent is extended or adjusted under 35 U.S.C. 154(b) by 264 days.

(21) Appl. No.: 15/576,716

(22) PCT Filed: May 26, 2016

(86) PCT No.: PCT/CA2016/050593
§ 371 (c)(1),
(2) Date: Nov. 23, 2017

(87) PCT Pub. No.: WO2016/187715
PCT Pub. Date: Dec. 1, 2016

(65) Prior Publication Data
US 2018/0132698 A1 May 17, 2018

Related U.S. Application Data

(60) Provisional application No. 62/166,534, filed on May 26, 2015.

(51) Int. Cl.
*A61B 1/00* (2006.01)
*A61B 5/00* (2006.01)
(Continued)

(52) U.S. Cl.
CPC ........ *A61B 1/0019* (2013.01); *A61B 1/00016* (2013.01); *A61B 1/00032* (2013.01);
(Continued)

(58) Field of Classification Search
CPC . A61B 1/0019; A61B 5/0071; A61B 1/00016; A61B 1/00032; A61B 1/00108;
(Continued)

(56) References Cited

U.S. PATENT DOCUMENTS

2016/0246255 A1* 8/2016 Brooker ................. G03H 1/06

FOREIGN PATENT DOCUMENTS

CA 2823561 A1 6/2012

OTHER PUBLICATIONS

Grewe et al. "Fast two-layer two-photon imaging of neuronal cell populations using an electrically tunable lens" Biomedical Optics Express, vol. 2, No. 7, pp. 2035-2046 (Year: 2011).*
(Continued)

*Primary Examiner* — George G King
(74) *Attorney, Agent, or Firm* — Norton Rose Fulbright Canada LLP; Reno Lessard

(57) ABSTRACT

There is disclosed an imaging system for use in imaging a sample. The imaging system comprising a light source and a light detector. A probe optically coupled to the imaging assembly. The probe being configured to, during use, direct light from the light source to a focal point to illuminate the sample, and from the focal point to the light detector. The probe having a tunable liquid crystal lens (TLCL) assembly comprising at least one pair of TLCLs, the TLCLs of the pair being superposed to one another, a gradient-index (GRIN) lens assembly having a base being optically connected to the TLCL assembly, and a tip opposite to the base. The focal point being at a working distance from the tip. The working distance being adjustable relative to the tip by tuning each TLCL of the TLCL assembly during use.

16 Claims, 15 Drawing Sheets

(51) Int. Cl.
*G02F 1/29* (2006.01)
*G02B 3/00* (2006.01)
*G01N 21/64* (2006.01)
*G02F 1/1347* (2006.01)
*G02B 3/14* (2006.01)
*A61B 1/06* (2006.01)
*A61B 1/04* (2006.01)
*G02F 1/1343* (2006.01)

(52) U.S. Cl.
CPC ...... *A61B 1/00108* (2013.01); *A61B 1/00165* (2013.01); *A61B 5/0042* (2013.01); *A61B 5/0068* (2013.01); *A61B 5/0071* (2013.01); *A61B 5/0084* (2013.01); *G01N 21/6458* (2013.01); *G01N 21/6486* (2013.01); *G02B 3/00* (2013.01); *G02B 3/0087* (2013.01); *G02B 3/14* (2013.01); *G02F 1/13471* (2013.01); *G02F 1/29* (2013.01); *A61B 1/04* (2013.01); *A61B 1/06* (2013.01); *A61B 2562/0242* (2013.01); *G01N 2021/6419* (2013.01); *G01N 2021/6441* (2013.01); *G01N 2021/6478* (2013.01); *G02F 1/134309* (2013.01); *G02F 2001/294* (2013.01); *G02F 2201/12* (2013.01)

(58) Field of Classification Search
CPC . A61B 1/00165; A61B 5/0042; A61B 5/0068; A61B 5/0084; A61B 1/04; A61B 1/06; A61B 2562/0242; G02F 1/133; G02F 1/13471; G02F 1/29; G02F 1/134309; G02F 2001/294; G02F 2201/12; G01N 21/6458; G01N 21/6486; G01N 2021/6419; G01N 2021/6441; G01N 2021/6478; G02B 3/00; G02B 3/0087; G02B 3/14
See application file for complete search history.

(56) References Cited

OTHER PUBLICATIONS

Bagramyan et al., "Motion-free endoscopie system for brain imaging at variable focal depth using liquid crystallenses", Journal of Biophotonics, vol. 1, Issue 13. Published online Mar. 9, 2016.
Yi-Hsin Lin et al., "Electrically Tunable Liquid Crystal Lenses and Applications", Molecular Crystals and Liquid Crystals, vol. 596, Issue I, pp. 12-21, Sep. 30, 2014.

* cited by examiner

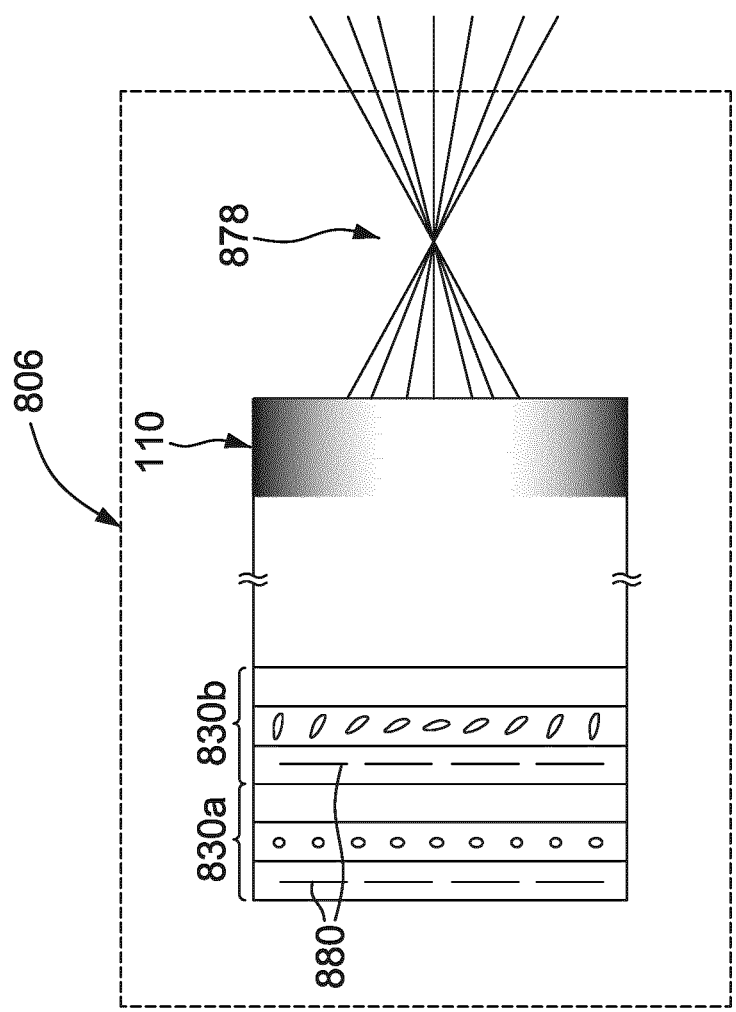
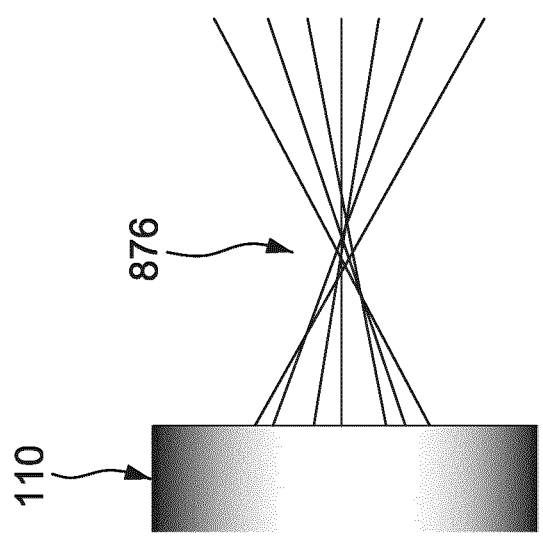
Fig. 8B
Fig. 8A

TUNABLE OPTICAL DEVICE, TUNABLE LIQUID CRYSTAL LENS ASSEMBLY AND IMAGING SYSTEM USING SAME

FIELD

The improvements generally relate to imaging systems and optical devices and more particularly to tunable imaging systems and optical devices.

BACKGROUND

Imaging systems that can image tissue at a given depth within biological tissue are useful in a multitude of medical applications. In these medical applications, the imaging system commonly used in the field has an imaging assembly optically coupled to a probe having an elongated imaging lens generally provided in the form of a gradient-index (GRIN) lens. The elongated imaging lens has a longitudinal axis defined between two opposite ends thereof. One end is coupled to the imaging assembly while the other end, referred to as the tip, is inserted within the biological tissue for imaging thereof. The typical imaging system has a fixed focal point spaced from the tip along the longitudinal axis such that imaging of the biological tissue is limited to the fixed focal point.

Another imaging system commonly used for such application incorporates a mechanical actuator to move optical components of the imaging assembly in order to vary the focal point of the imaging system in the biological tissue. While allowing to image the biological tissue at a varying focal, such imaging systems suffer from drawbacks inherent to the presence of the mechanical actuator. Such drawbacks can be particularly significant in vivo applications, and more particularly for free-behaving animal experiments. There thus remains room for improvement.

SUMMARY

There is disclosed an imaging system including a tunable optical device which has a tunable liquid crystal lens (TLCL) assembly, a gradient-index (GRIN) lens assembly having a base optically connected to the TLCL assembly, and a tip opposite the base. The tunable optical device defines a focal point at a working distance from the tip, and the working distance is adjustable by tuning the TLCL assembly.

In accordance with an aspect, there is provided an imaging system for use in imaging a sample comprising: an imaging assembly comprising a light source and a light detector; and a probe optically coupled to the imaging assembly, the probe being configured to, during use, direct light from the light source to a focal point to illuminate the sample, and from the focal point to the light detector, the probe comprising: a TLCL assembly comprising at least one pair of TLCLs, the TLCLs of the pair being superposed to one another, a GRIN lens assembly having a base being optically connected to the TLCL assembly, and a tip opposite to the base, the focal point being at a working distance from the tip, the working distance being adjustable relative to the tip by tuning each TLCL of the TLCL assembly during use.

In accordance with another aspect, there is provided a TLCL assembly comprising an optical axis and one pair of TLCLs each superposed one to the other, wherein one TLCL of the pair is rotated by 180 degrees about the optical axis with respect to the other TLCL of the pair.

In accordance with another aspect, there is provided a tunable optical device for interrogating a sample, the tunable optical device comprising: a GRIN lens assembly; and at least one segmented TLCL optically connected to the GRIN lens assembly, the at least one segmented TLCL having an annularly segmented electrode, the annularly segmented electrode having a number of electrode segments being independently drivable to compensate for aberrations of at least one of the GRIN lens assembly and the sample.

It is understood that while being useful in an imaging system, the tunable optical device and the TLCL assembly can be used in optical systems (non-imaging systems for interrogating a sample) other than the exemplary imaging system described herein. Such optical systems and many further features and combinations thereof concerning the present improvements will appear to those skilled in the art following a reading of the instant disclosure.

DESCRIPTION OF THE FIGURES

In the figures,

FIG. 8A is a partial side view of an example of a tip of a probe, showing aberrations;

FIG. 8B is a schematic, and partial side view of another example of a probe, focusing at a focal point with corrected aberrations;

These drawings depict example embodiments for illustrative purposes, and variations, alternative configurations, alternative components and modifications may be made to these example embodiments.

DETAILED DESCRIPTION

Figure 1:
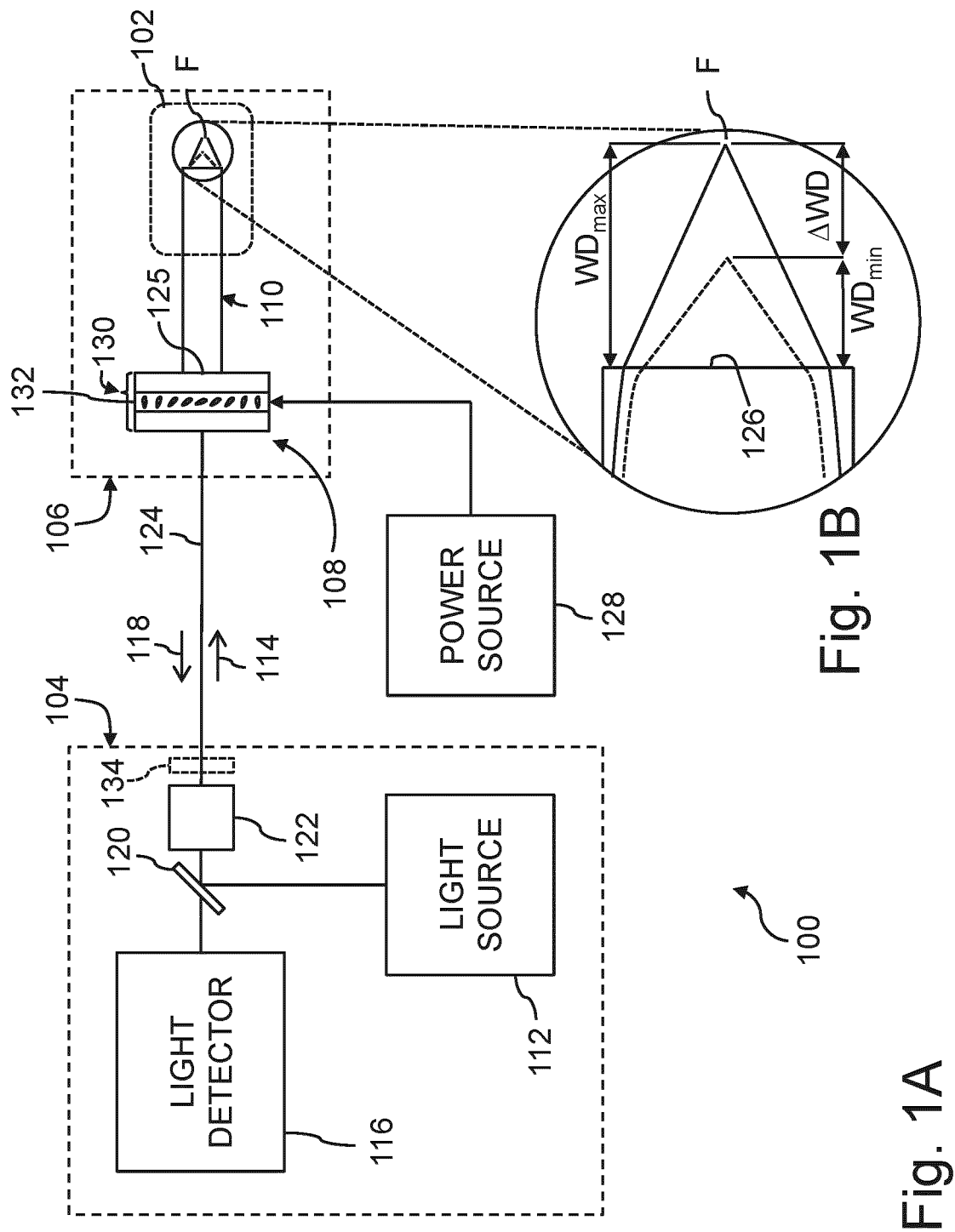
FIG. 1A is a schematic view of an example of an imaging system.
FIG. 1B is an enlarged view of a portion of the imaging system of FIG. 1A.

FIG. 1A shows an example of an imaging system 100 that can be used for imaging a specimen 102, in accordance with an embodiment.

As shown, the imaging system 100 has an imaging assembly 104 optically coupled to a tunable optical device or probe 106. The probe 106 has a tunable liquid crystal lens (TLCL) assembly 108, a gradient-index (GRIN) lens assembly 110 (also referred to as "imaging GRIN lens assembly 110") having a base 125 optically connected to the TLCL assembly 108, and a tip 126 opposite the base 125.

As depicted, the imaging assembly 104 has a light source 112 and a light detector 116 coupled to the probe 106. The probe 106 is configured to, during use, direct light generated by the light source 112 to a focal point F to illuminate the specimen 102 along direction 114 and from the focal point F to the light detector 116 along direction 118.

As best seen in FIG. 1B, the focal point F is at a working distance WD from the tip 126. During use, the working distance WD is adjustable relative to the tip 126 by tuning each TLCL of the TLCL assembly 108. As shown, the working distance associated with the focal point F can be adjusted from $WD_{min}$ to $WD_{max}$ (yielding an adjustability range of $\Delta WD$) by suitable tuning of the TLCL assembly 108.

Such tuning of the TLCL assembly 108 can avoid moving mechanical parts such as mechanical actuators and the like and may not cause any image deformation since the focus of the imaging GRIN lens assembly 110 is adjusted by the TLCL assembly 108.

Referring back to the embodiment of FIG. 1A, the light generated by the light source 112 is coupled into the probe 106 using a dichroic mirror 120 that reflects the light into an objective lens 122 which, in turn, injects the light into a waveguide 124 (also referred to as "coupling waveguide 124") optically coupled to the probe 106. Once illuminated, imaging beams associated with the specimen 102 are propagated along an imaging path which follows the probe 106, the coupling waveguide 124, the objective lens 122 and the dichroic mirror 120 towards the light detector 116. The imaging assembly 104 shown in FIG. 1A is only exemplary, other suitably imaging assemblies can be deemed fit by one skilled in the art.

As will be understood, the TLCL assembly 108 is typically tuned by modifying a driving signal provided thereto via a power source 128. To do so, the power source 128 is electrically connected to electrodes (not shown) of the TLCL assembly 108. Modifying the driving signal can include modifying its frequency, its amplitude, its voltage, and/or any combination thereof. In some embodiments, the TLCL assembly 108 can be tuned to react with a temporal response which ranges from 10 ms (e.g., using a rapid frequency modulation protocol) to 1000 ms.

The optical connection between the TLCL assembly 108 and the GRIN lens assembly 110 can be obtained by fixedly connecting the TLCL assembly 108 to the GRIN lens assembly 110 by using a suitable connector such as a mount or glue, for instance.

As illustrated, the TLCL assembly 108 shown in FIG. 1A has one TLCL 130. The liquid crystal (LC) is a birefringent material such that incident light passing through a LC layer 132 of the TLCL can be analyzed as two orthogonal light polarizations. The single TLCL 130 shown in FIG. 1A thus focuses a single polarization of light and leaves the other orthogonal polarization essentially unaffected, such a TLCL assembly 108 is said to be polarization dependent. In this embodiment, the light source 112 can be polarized or the imaging assembly 104 can have an optional polarizer 134 in order to limit either the incident light or the emitted light (i.e. light emitted from the specimen 102) to only one polarization, which corresponds to the polarization of the single TLCL 130.

As will be detailed herein, the TLCL assembly 108 can have one TLCL or more than one TLCL (e.g., two, four or more TLCLs). When the TLCL assembly 108 comprises more than one TLCL, the TLCLs are superposed to one another such that incident light can propagate through each of the TLCLs of the assembly 108 in a serial manner. In other words, the TLCLs are stacked to one another so that the apertures of the TLCLs face each other and are aligned along an optical axis of the probe. Further, the GRIN lens assembly 110 can have a single GRIN lens, or any combination of GRIN elements (e.g., guiding GRIN rod, collimating GRIN lens, focusing GRIN lens).

Figure 2:
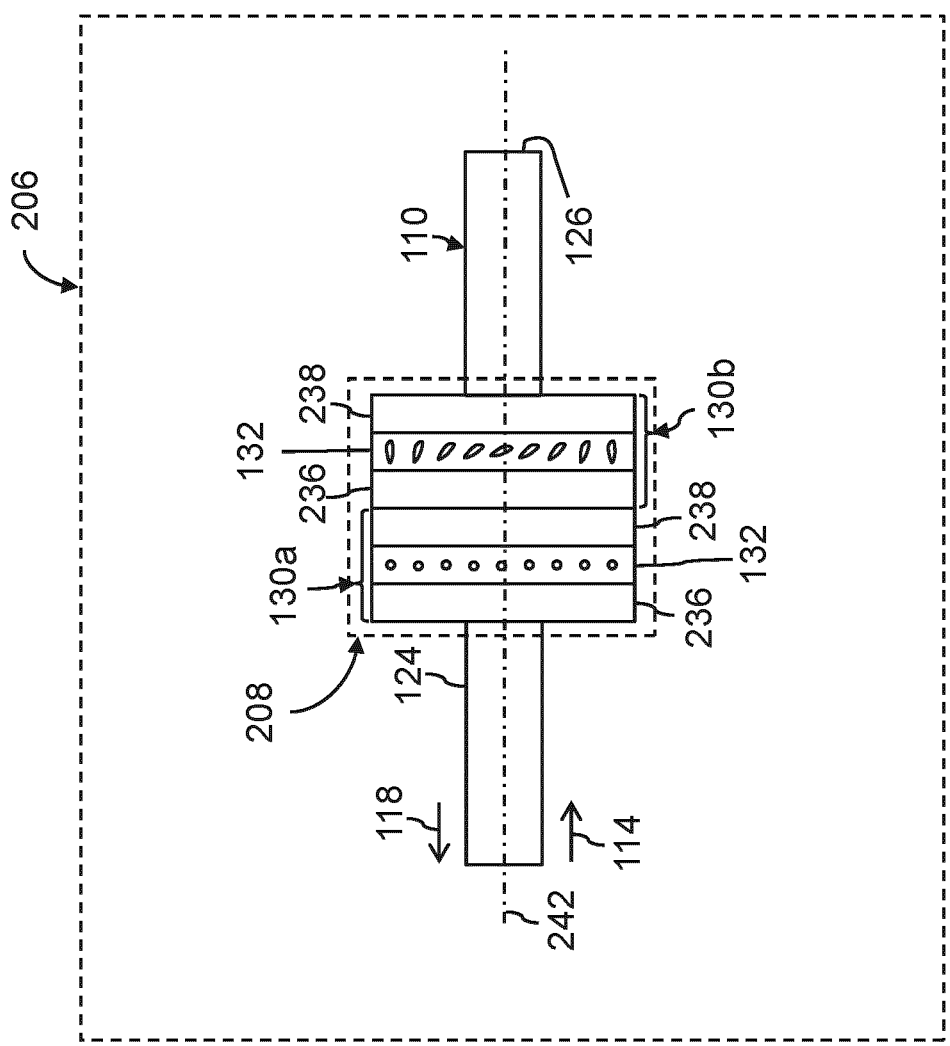
FIG. 2 is a schematic view of an example of a probe, with two TLCLs in a polarization independent configuration.

FIG. 2 shows another example of a probe 206. As illustrated, the probe 206 has a TLCL assembly 208 having a pair of TLCLs (first and second TLCLs 130a and 130b) and is said to be "polarization independent", as will be explained in the following paragraph. The pair of TLCLs 130a and 130b is positioned between the coupling waveguide 124 such as a GRIN waveguide or an optical-fiber and the GRIN lens assembly 110. In the illustrated embodiment, the light from the light source 112 propagates along the direction 114 while light from a specimen, during use, propagates along the direction 118. As it may be readily understood, each TLCL 130 has the LC layer 132 comprised between a first face 236 and a second face 238. When the TLCL assembly 208 has more than one TLCL, the TLCLs 130a and 130b are superposed, or stacked, on one another by abutting the first face 236 of the second TLCL 130b on the second face 238 of the adjacent, first TLCL 130a. Such abutting may include fixing two adjacent TLCLs with an optical glue. Such an optical glue can also be used to optically couple the TLCL assembly to the imaging GRIN lens assembly and/or the coupling GRIN waveguide, for instance.

The probe 206 shown in FIG. 2 is in a polarization independent configuration. Indeed, since LC is a birefringent material, addressing the two orthogonal polarization of the incident light propagating along an optical axis 242 is of importance. This is achieved by positioning each TLCL 130a and 130b of the pair such that each TLCL acts on a different orthogonal polarization of the light in order to render the probe 206 independent of the polarization of the incident light. In other words, still referring to FIG. 2, the LCs of the leftmost TLCL 130a have an orientation (through the page) perpendicular to an orientation of the LCs of the rightmost TLCL 130b (along the page). Providing the TLCL assembly 208 in the polarization independent configuration is preferred in situations where the light source 112 is polarized in more than one polarization. Indeed, in circumstances where the light source 112 is a white electroluminescent diode (LED), the white light contains a chaotic mixture of polarizations (which can be represented as a sum of the two orthogonal polarizations), and a polarization independent TLCL assembly 208 is required to focus the light along the two orthogonal polarizations.

Figure 3:
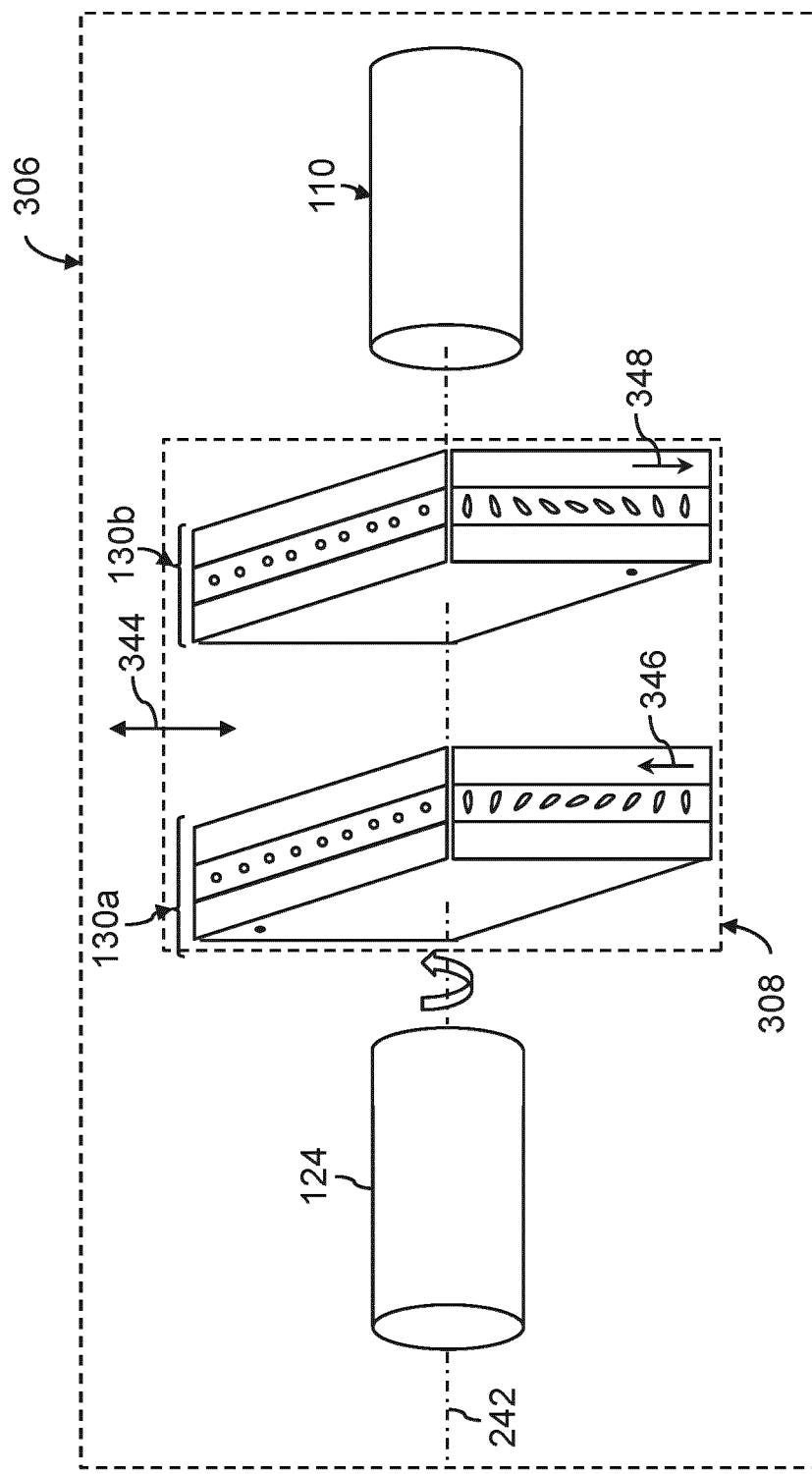
FIG. 3 is an oblique and exploded view of another example of a probe, with two
TLCLs in an aberration compensation configuration.

FIG. 3 shows an exploded view of a probe 306 having the coupling waveguide 124 (e.g., GRIN rod), a TLCL assembly 308 and the imaging GRIN lens assembly 110. As depicted, the imaging GRIN lens assembly 110 generally has an elongated, cylindrical shape but can have any suitable shape. Such a TLCL assembly 308 is said to be systematic aberrations independent or compensated. As depicted, the TLCL assembly 308 has a pair of TLCLs (first and second TLCLs 130a and 130b) wherein the first TLCL 130a is rotated by a half-rotation (i.e. 180 degrees) about the optical axis 242. As it may be readily understood, the probe 306 shown in FIG. 3 has an increased optical power compared to the probe 106, shown in FIG. 1A, having only one TLCL 130, for instance. As opposed to the probe 206 shown in FIG. 2, the probe 306 is not polarization independent so polarizing the emitted light, polarizing the incident light or using a polarized light source is required. Indeed, even if two different TLCL assemblies have a corresponding number of TLCLs, the way the TLCLs are superposed one to the other dictates the function that the resulting TLCL assembly will perform (i.e. polarization independent and/or systematic aberrations independent).

The configuration shown in FIG. 3 is referred to as an aberration compensation configuration (or systematic aberrations independent) since it helps reducing the effect of systematic aberrations (e.g., coma) that are generated during the manufacture of the TLCLs.

In context, the manufacture process of the TLCLs typically begins with the production of an optical wafer upon a series of manufacturing steps. Once the optical wafer is diced into a multitude of separate TLCLs, TLCLs associated with the same optical wafer are typically characterized by similar systematic aberrations. Accordingly, providing the TLCL assembly 308 with two TLCLs 130a and 130b having similar systematic aberrations adjacent but rotated by 180 degrees from one another helps compensating for these systematic aberrations. For example, knowing that the two TLCLs 130a and 130b have similar systematic aberrations causing a coma aberration along a transverse orientation 344, if the two TLCLs 130a and 130b are positioned in the aberration compensation configuration described above (the first TLCL 130a is rotated of 180 degrees about the optical axis 242 with respect to the second TLCL 130b), each TLCL will cause the incident light to be modified by the (same) coma aberration but in two opposing directions 346 and 348 such that the coma aberration is substantially canceled out. It is noted that the aberration compensation provided by the aberration compensation configuration is not limited to the coma aberration but can extend to other types of aberrations.

It was found that such systematic aberrations become more significant as the nominal diameter of the TLCL decreases. More specifically, TLCLs having a nominal diameter of less than 1 mm, preferably 0.5 mm, are especially useful in vivo since the GRIN lens assembly is less damageable due to its reduced footprint. With the TLCLs and the GRIN lens assembly having such nominal diameters, positioning the TLCLs in the aberration compensation configuration is thus preferred. Accordingly, the imaging GRIN lens assembly 110 can have a nominal diameter of 1 mm or less, preferably 0.5 mm. Providing such a small nominal diameter may help reduce damage to biological tissue occurring when inserting the imaging GRIN lens assembly 110 in the biological tissue. In some embodiments, the length of the GRIN lens assembly 110 is more than 2 mm, preferably 7 mm.

Figure 4A:
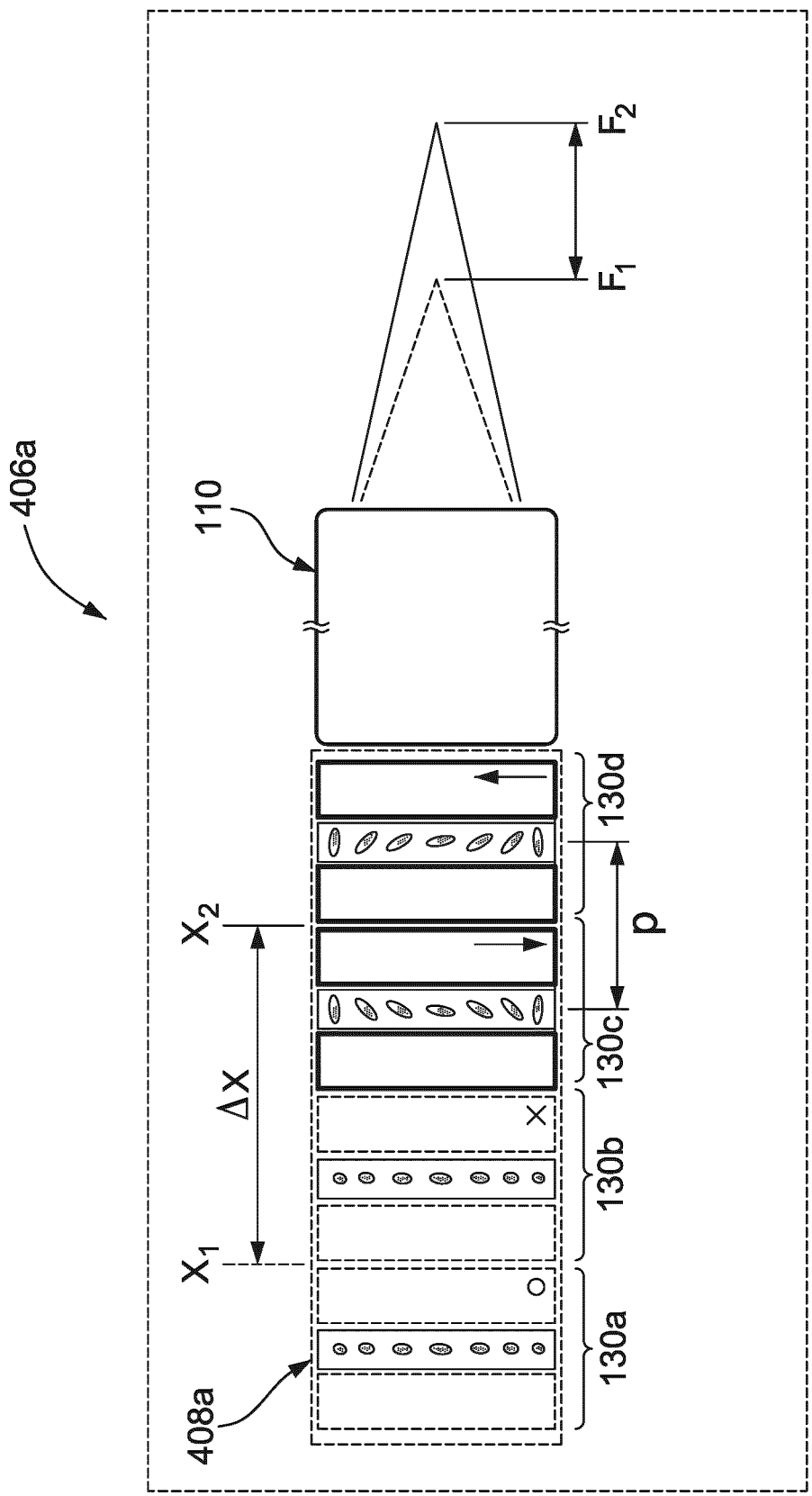
FIG. 4A is a schematic view of another example of a probe, with four TLCLs in a first aberration compensation configuration.
Figure 4B:
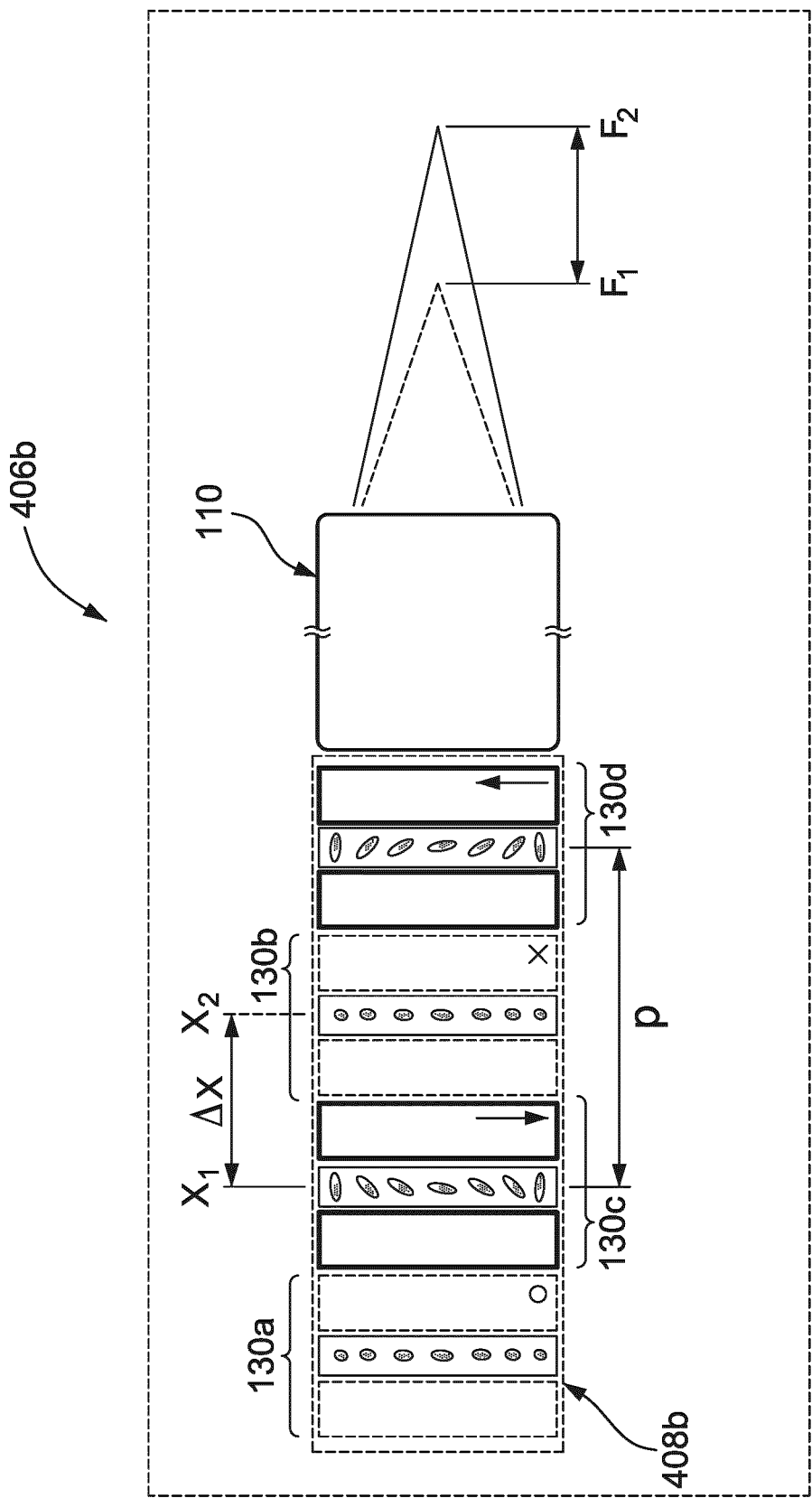
FIG. 4B is a schematic view of another example of a probe, with four TLCLs in a second aberration compensation configuration.
Figure 4C:
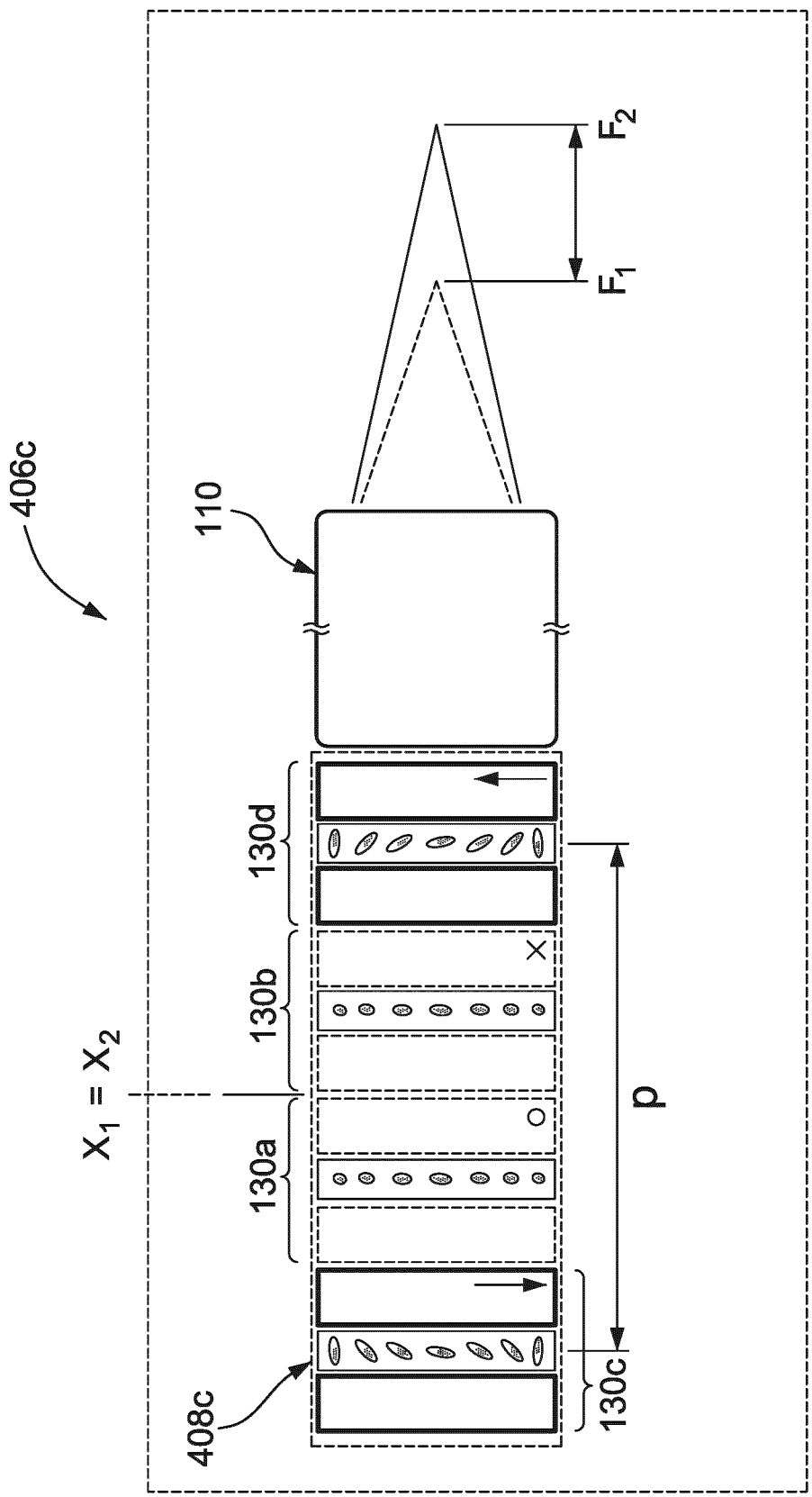
FIG. 4C is a schematic view of another example of a probe, with four TLCLs in a third aberration compensation configuration.

FIGS. 4A-C show examples of probes 406a, 406b and 406c wherein the TLCL assemblies 408a, 408b and 408c each have two pairs of TLCLs configured to render the probe both polarization independent and free from the systematic aberrations mentioned above as well as to enhance the optical power of the probes. For ease of reading, first and second TLCLs of the first pair are shown at 130a and 130b and third and fourth TLCLs of the second pair are shown at 130c and 130d throughout FIGS. 4A-C. Some other configurations of the probe having two pairs of TLCLs are possible, the embodiments shown in FIGS. 4A-C are only examples. Before specifically describing FIGS. 4A-C, it should be understood that the configuration of the TLCLs of the TLCL assembly can influence the performances of the TLCL assembly as a whole. Indeed, a focal point mismatch between a first focal point of one orthogonal polarization and a second focal point of the other orthogonal polarization of the incident light can be reduced or increased depending on how the TLCLs are distanced to one another. Further, the configuration of the TLCLs can influence the way the systematic aberrations are compensated also. More specifically, as will be understood by the reading of the following paragraphs and referring to FIGS. 4A-C, the focal point mismatch ($F_2$-$F_1$) between the two orthogonal polarizations of the light is proportional to the spacing distance Δx. Additionally, the systematic aberrations compensation are inversely proportional to the TLCL interval p, i.e. the distance between two TLCLs associated with one of two orthogonal polarizations of the light which are rotated by 180 degrees with one another about the probe axis.

FIG. 4A shows the probe 406a wherein the two TLCLs of each pair are adjacent from one another. The first pair of TLCLs 130a and 130b acts on a first polarization and is configured in a systematic aberrations compensation configuration. The second pair of TLCLs 130c and 130d acts on a second polarization, orthogonal to the first polarization and is configured also in a systematic aberrations compensation configuration. In the illustrated embodiment, the spacing distance Δx between a first median position $x_1$ of the TLCLs acting on the first polarization and a second median position $x_2$ of the TLCLs acting on the second polarization is maximized. Such a spacing distance, $\Delta x = x_2 - x_1$, causes a focal point $F_1$ associated with the first polarization and a focal point $F_2$ associated with the second polarization to be increased. However, in this configuration, the systematic aberration compensation (e.g., coma compensation) is optimized since the TLCL interval p, which separates the two TLCLs of the first and the second pair, is minimal, i.e. the two TLCLs of each pair are immediately adjacent from one another. Following a Zemax™ simulation, $F_1$ can differ from $F_2$ by about 5±1 μm, for instance, when the spacing distance Δx is 480 μm and the TLCL interval p is 240 μm. In this exemplary simulation, the TLCLs are set to a thickness of 40 μm, a nominal diameter of 0.5 mm and a nominal optical power of 350 diopters; a GRIN rod 1210 (see FIG. 12) that is set to a nominal diameter of 0.5 mm, a numerical aperture of 0.2, a pitch of 0.5; and the imaging GRIN lens assembly 110 is set to have a nominal diameter of 0.5 mm, a numerical aperture of 0.5 and a pitch of 0.23. As will be understood by the skilled reader, a ray incident on a GRIN lens follows a sinusoidal path therealong. The pitch of the GRIN lens is the fraction of a full sinusoidal period that the ray traverses in the lens. For instance, a GRIN lens with a pitch of 0.25 has a length equal to ¼ of a sine wave, which would collimate a point source at the surface of the GRIN lens.

FIG. 4B shows the probe 406b wherein the first and the second TLCLs 130a and 130b of the first pair are interspersed with the third and the fourth TLCLs 130c and 130d of the second pair. In the illustrated embodiment, the spacing distance Δx between the first and the second median positions is reduced and the TLCL interval p is increased compared to the embodiment shown in FIG. 4A. The reduced spacing distance Δx yields a smaller difference between the first and the second focal points $F_1$ and $F_2$, but this is at the expense of the systematic aberration compensation which is less optimized. Indeed, the systematic aberrations that are caused by the third TLCL 130c are propagated along a longer TLCL interval p so that the fourth TLCL 130d is less capable of compensating the so-called "propagated systematic aberrations". This applies for the first pair of TLCLs 130a and 130b also. In another Zemax™ simulation having similar simulation parameters than for the simulation shown in FIG. 4A, the difference between the first and the second focal points $F_1$ and $F_2$ is simulated to be 2.5±1 μm when the spacing distance Δx is 240 μm and the TLCL interval p is 480 μm.

FIG. 4C shows the probe 406c wherein the first pair of TLCLs 130a and 130b is sandwiched between the third and the fourth TLCLs 130c and 130d of the second pair. In this embodiment, the difference between the first and the second focal points $F_1$ and $F_2$ is optimized since the spacing distance Δx vanishes while the systematic aberrations are even less compensated than for the embodiment shown in FIG. 4B. Indeed, in still another Zemax™ simulation having similar simulation parameters than for the simulation shown in FIG. 4A, the difference between the first and the second focal points $F_1$ and $F_2$ is simulated to be 0±1 μm when the spacing distance Δx is null and the TLCL interval p is 720 μm.

Still referring to FIGS. 4A-C, it is understood that the focal point mismatch between $F_1$ and $F_2$ caused by the spacing distance Δx can be overcome by modulating each pair of TLCLs separately. With such a modulation, the focal point mismatch (e.g., $F_1-F_2 \neq 0$) can be minimized while optimizing the systematic aberration compensation. Further, chromatic aberration can be corrected in a similar manner. Indeed, since each wavelength focuses at a different focal point (e.g., $F_{\lambda 1} \neq F_{\lambda 2}$), the chromatic aberration can be corrected by modulating each pair of TLCLs separately.

Figure 5:
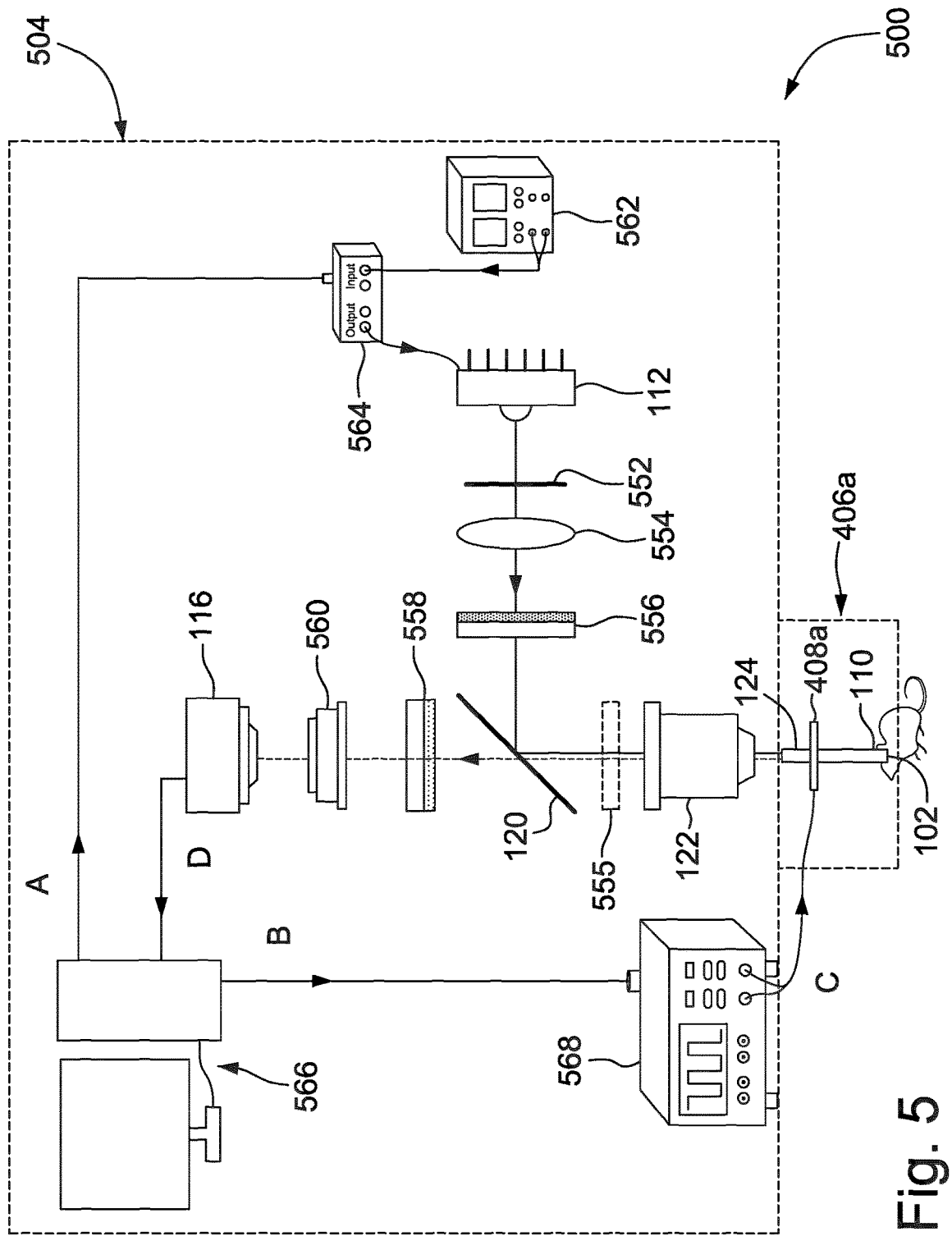
FIG. 5 is a schematic view of another example of an imaging system.

FIG. 5 is a schematic view of an example of an imaging system 500 for imaging biological cells in the brain tissue having fluorescent molecules therein, in accordance with an embodiment. As shown, the imaging system 500 has an imaging assembly 504 which is optically coupled to the "endoscope" probe 406a. As described above, the TLCL assembly 408a has two pairs of TLCLs to render the TLCL assembly 408a polarization independent and free from the systematic aberrations (as described above). The probe 406a has the coupling waveguide 124 provided opposite the imaging GRIN lens assembly 110 with respect to the TLCL assembly 408a. The illumination path of the imaging system 500 starts at the light source 112 which is a white LED in the illustrated embodiment. The white light is diffused and condensed by a diffuser 552 and a condenser 554 disposed along the illumination path, proximate the light source 112. The illumination light is filtered by an excitation filter 556 which lets pass wavelengths substantially corresponding to an excitation wavelength of the fluorescent molecules and filters out other wavelengths. The remaining excitation wavelength is reflected through the dichroic mirror 120 towards the objective lens 122 which is used to inject the excitation wavelength into the coupling waveguide 124 towards the specimen 102 (e.g., biological brain tissue). Once excited at the excitation wavelength, the fluorescent molecules of the biological brain tissue emit a fluorescence signal which is collected by the probe 406a. The imaging path of the imaging system 500 passes through the probe 406a, back to the objective lens 122, through the dichroic mirror 120, through an emission filter 558 towards the light detector 116. The emission filter typically lets pass the fluorescence signal while filtering out light associated with the excitation wavelength. In the illustrated embodiment, a tube lens 560 is optionally provided between the emission filter 558 and the light detector 116. In this example, the light detector 116 is a charge-coupled device (CCD) camera which images the biological brain tissue. In another embodiment, the imaging system 500 can have optional polarization control elements 555 positioned between the probe 406a and the dichroic mirror 120. The polarization control elements 555 (e.g., linear and/or circular polarizers or wave plates) are used in order to enable the use of the imaging system 500 for polarization discrimination imaging.

Still referring to FIG. 5, the light source 112 is powered by a current generator 562 and is triggered by a triggering device 564. In this embodiment, the triggering device 564 is connected to a computer 566 which sends triggering instructions A to the triggering device 564 in order to operate the light source 112 for only given period of time (e.g., five minutes). Such triggering instructions A prevent from overheating or damaging the biological tissue. The computer 566 sends tuning instructions B in order to tune a function generator 568 at a given electrical function C having a given tension, frequency and phase modulation. The given electrical function C acts on the electrodes of each of the TLCLs of the TLCL assembly 408a in order to adjust more or less the working distance of the probe 406a. In this embodiment, the frequency of the given electrical function C determines the working distance at which the probe 406a focuses (e.g., the tension is constant). During use, the light detector 116 communicates images D to the computer 566 which can display the images suitably to a user for instance. In this embodiment, it is understood that the triggering instructions A, the tuning instructions B and the given electrical function C are controlled by the computer 566 using a suitable program such as LabVIEW™, for instance.

Figure 6A:
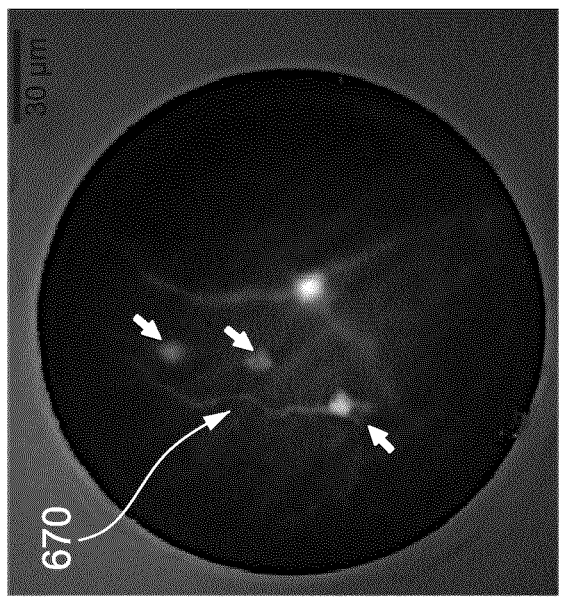
FIGS. 6A-D are images taken, using the imaging system of FIG. 5, at four different working distances inside a specimen.
Figure 6B:
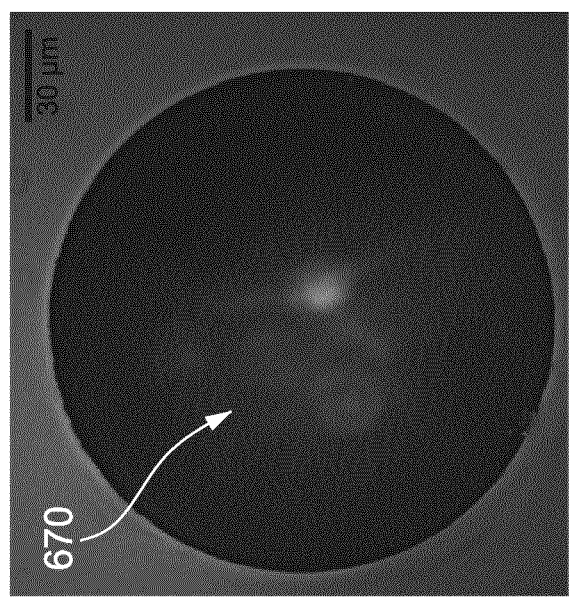
Figure 6C:
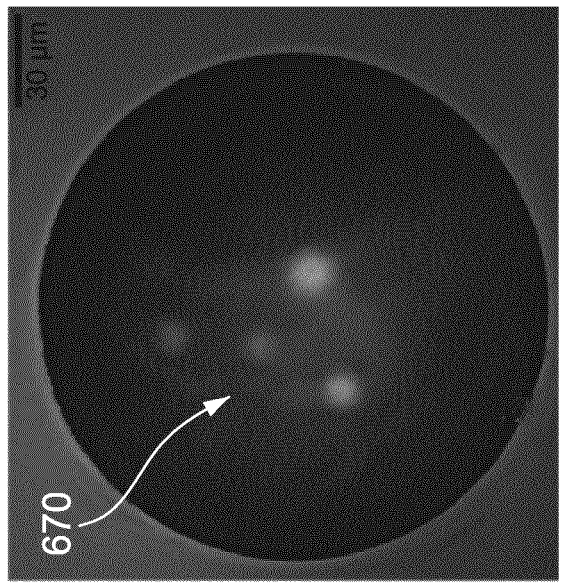
Figure 6D:
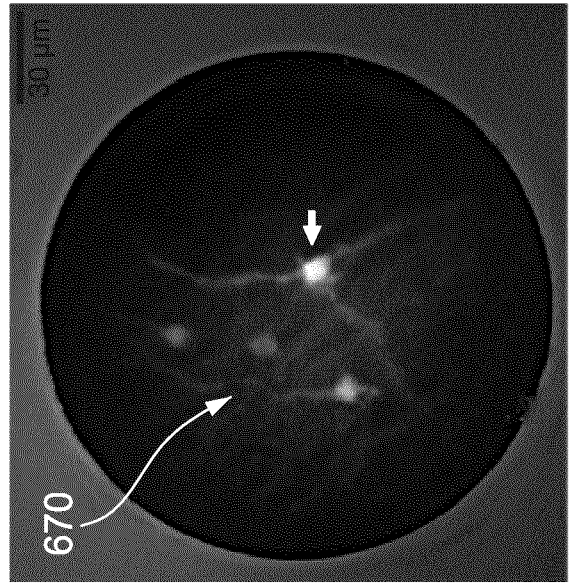
Figure 10:
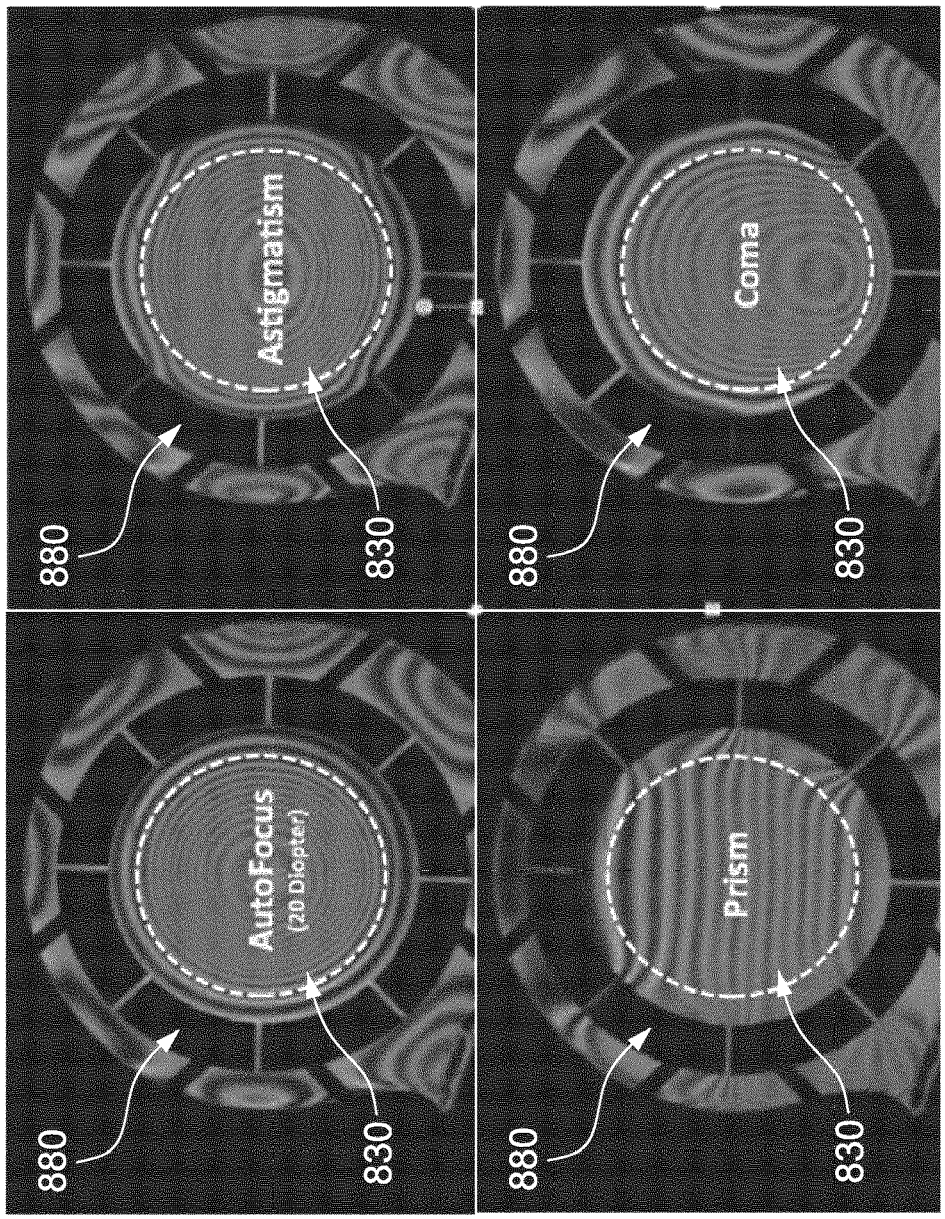
FIG. 10A is a top plan view of an example of a segmented TLCL tuned to autofocus.
FIG. 10B is a top plan view of an example of a segmented TLCL tuned to correct an astigmatism aberration.
FIG. 10C is a top plan view of an example of a segmented TLCL tuned to correct a prism aberration.
FIG. 10D is a top plan view of an example of a segmented TLCL tuned to correct a coma aberration.
Figure 11:
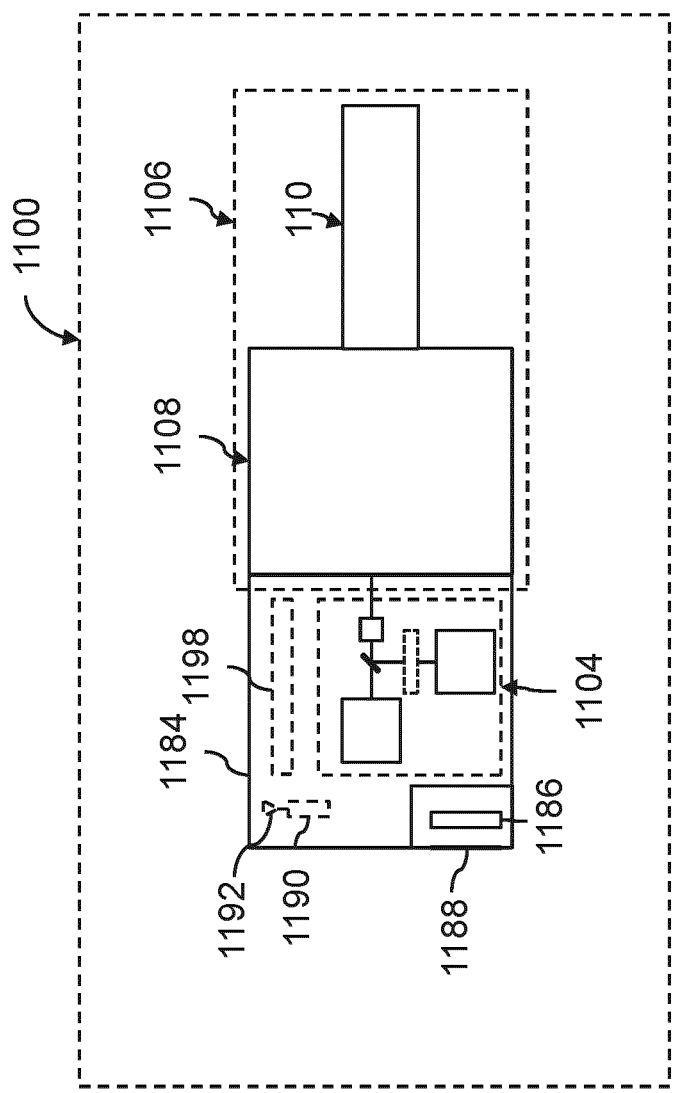
FIG. 11 is a schematic view of an example of a standalone imaging system.

FIGS. 6A-D show exemplary images of olfactory bulb granule cells 670 in the brain tissue of a mouse, in accordance with an embodiment. In this example, the frequency of the given electrical function C tuning the TLCL assembly is: 1 kHz which yields a reference focal point as seen in FIG. 6A, 10 kHz which yields a focal point 22 μm shallower than the reference focal point as seen in FIG. 6B, 11 kHz which yields a focal point 26 μm shallower than the reference focal point as seen in FIG. 6C, and 15 kHz which yields a focal point 41 μm shallower than the reference focal point as seen in FIG. 6D. As it can be seen, working distance adjustability in neuroimaging applications is useful due to the complex three dimensional nature of the neurons.

Figure 7B:
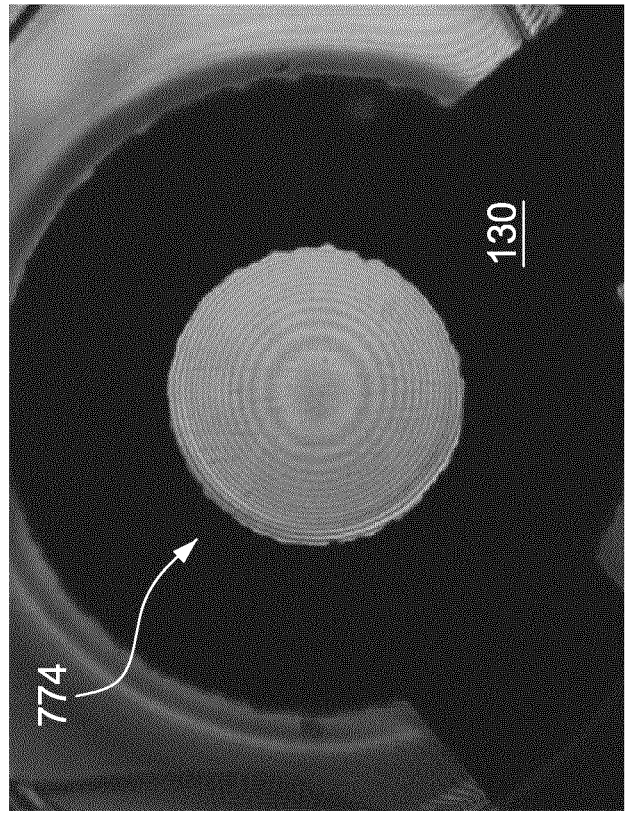
FIG. 7B is a top plan view of a TLCL as seen through a polarimetric system, showing a corrected coma aberration, in accordance with an embodiment.
Figure 7A:
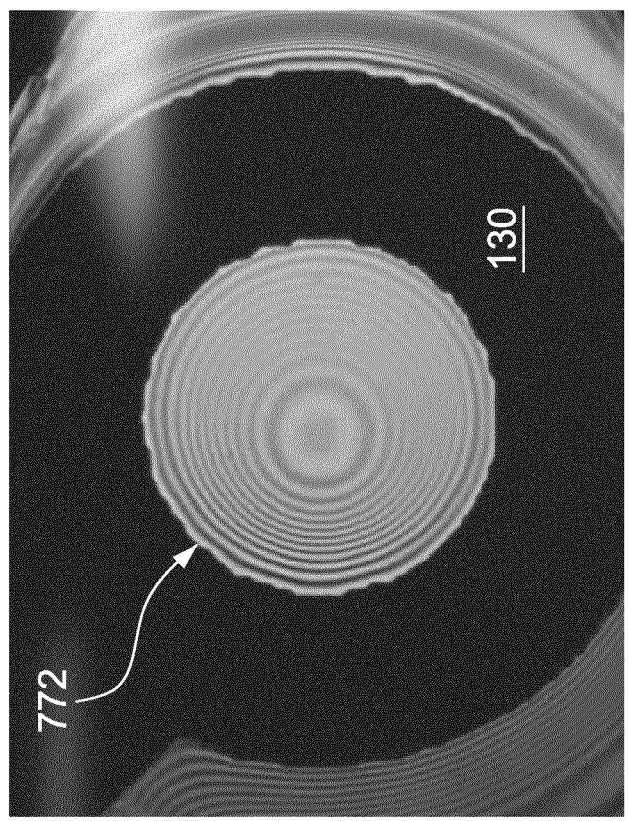
FIG. 7A is a top plan view of a TLCL as seen through a polarimetric system, showing a coma aberration, in accordance with an embodiment.

FIG. 7A shows an example of an image, seen through a polarimetric system such as two crossed polarizers and an interference filter, of a TLCL 130 with systematic aberrations such as a coma aberration 772 for an uncompensated TLCL assembly. FIG. 7B shows an example of an image of a TLCL 130 with a compensated coma aberration 774, also seen through a polarimetric system, when using the TLCL assembly in the aberration compensation configuration as indicated in the TLCL assembly 408a.

In some embodiments, a TLCL can be driven with a driving voltage of 2.4 V. This may be achieved by providing its electrodes on each side of the crystal layer or, in other words, by providing one of the two electrodes sandwiched between the first face and the crystal layer, and by providing the other one of the two electrodes sandwiched between the second face and the crystal layer. In some other embodiments, the TLCL can be driven by a driving voltage of 24 V. In some embodiments, each TLCL has an optical power of 320 diopters.

Figure 9:
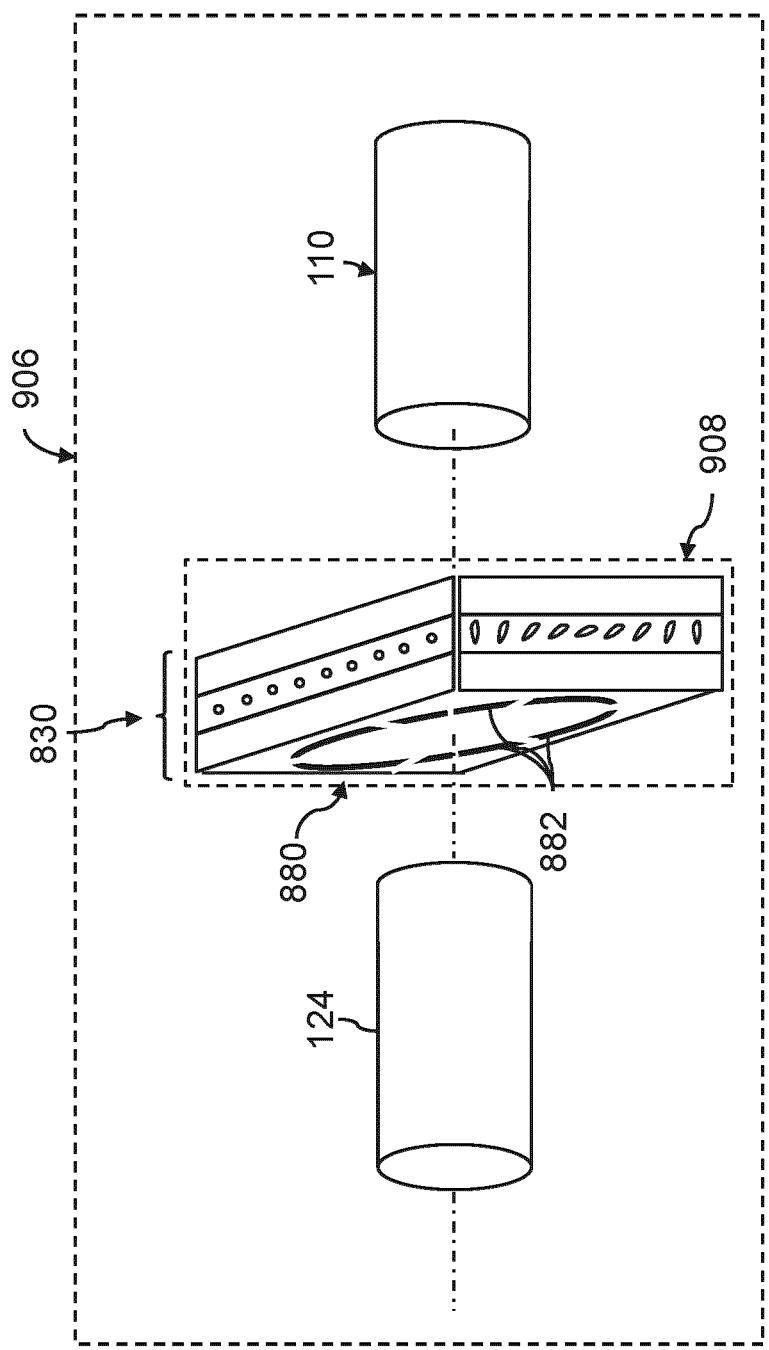
FIG. 9 is an oblique, exploded view of another example of a probe, with one segmented tunable liquid crystal lens.

FIG. 8A shows an example of the GRIN lens assembly 110 and its associated inherent aberrations 876 which can reduce the resolution of the image taken by the imaging system, for instance. FIG. 8B shows an example of a probe 806 where the inherent aberrations caused by the GRIN lens assembly 110 are corrected (see corrected aberrations 878) using the TLCL assembly in accordance with an embodiment. To do so, the TLCLs is provided in the form of segmented TLCLs 830a and 830b. Such a segmented TLCL has one of its electrode being embodied as an annularly segmented electrode 880, which is best shown in FIG. 9. It is understood that the probe 806 can have one or more than one TLCL each superposed one to the other and that each of the one or more than one TLCL of the embodiments described herein can be segmented TLCLs. Referring back to FIG. 8B, the segmented TLCLs 830a and 830b are used to correct aberrations of the optical system dynamically (e.g., in real-time) in order to enhance the resolution of the imaging system.

FIG. 9 shows an exploded view of a probe 906 having a segmented TLCL 830. The annularly segmented electrode 880 has a plurality of electrode segments 882 which are operable independently. Each of the electrode segments 882 is operable by the power source in function of a given tension, a given frequency and/or a given phase modulation. In an embodiment, the electrode segments 882 are independently drivable by the power source which is controlled by the computer 566. The computer 566 can have a memory on which is stored an aberration compensation program which is configured to compensate for aberrations of the probe 906 (e.g., TLCL assembly 908, the coupling waveguide 124, the imaging GRIN lens assembly 110) as well as to compensate for aberrations caused by the specimen. In cases where the specimen is a living organism, the aberration compensation program can compensate for aberrations due to movement of the living organism such as breathing or walking, for instance, in free-behaving animals applications. In other words, the imaging system is adapted to drive the segmented TLCLs 830 in order to compensate, dynamically, for aberrations caused by the optical components of the imaging system (non-living matter) and by the specimen (living matter) which are involved.

It was found that while increasing the number of electrode segments 882 generally allows a greater control on the aberration correction, it also generates an undesirable fringing field of a greater importance. Suitably selecting the number of electrode segments 882 of the annularly segmented electrode 880 is preferred. In an embodiment, the annularly segmented electrode 880 has four or eight electrode segments 882. Other number of electrode segments can also be used.

In another embodiment, the segmented TLCLs 830 are incorporated in an imaging system similar to the one shown in FIG. 5. In this specific embodiment, the specimen is excited with different excitation wavelengths such that more than one fluorescent molecule types are excited simultaneously. This can yield a fluorescence signal incorporating different emission wavelengths which can be imaged using the light detector. In such an embodiment, the segmented TLCLs 830 can be used to correct chromatic aberrations due to the different excitation wavelengths as well as aberrations due to the different emission wavelengths (non-segmented TLCLs 130 can also be used to correct chromatic aberrations, as mentioned above). In other words, by using the segmented TLCLs 830, the different excitation wavelengths can be focused at the same focal point in the specimen (and/or the different emission wavelengths can be focused on the light detector 116) such that the chromatic aberrations are corrected in the imaging system. In another embodiment, optional segmented TLCLs can be provided near the light source in order to correct aberration of the light source 112 and to control the emission wavelengths. In still another embodiment, optional electrically-controllable polarizers are provided near the light source 112 and the light detector 116 in order to actively control the polarization of the light which is emitted by the light source 112 and the light which is detected by the light detector 116. It is understood that the imaging system described herein is not limited to fluorescence and can also be used in Raman spectroscopy and other types of spectroscopy.

FIGS. 10A-D show the segmented TLCL 830 having the annularly segmented electrode 880, in accordance with some embodiments. Respectively, the segmented TLCL 830 can be used for autofocusing (e.g., 20 diopters) and also for aberration compensation such as astigmatism, prism, coma as shown throughout FIGS. 10A-D. Spherical and defocus aberrations can also be compensated. Such a segmented TLCL 830 is described in U.S. Patent Application Publication Number 2013/0250197 to Khodadad et al., the entire content of which is incorporated herein by reference.

FIG. 11 is a schematic, sectional view of an imaging system 1100, in accordance with another embodiment. In this illustrated embodiment, the imaging system 1100 is meant to be a wireless, self-powered, "miniature" and standalone device. An exemplary application of such an imaging system 1100 can be to image biological tissue of a free-behaving subject while avoiding wires such as electrical wires to control the light source, the light detector and the TLCL assembly 1108 or optical-fibers to carry the measured signal to a remote light detector, for instance. Indeed, the imaging assembly 1104 is enclosed in a probe module 1184 which is directly mounted to the probe 1106. As depicted, the probe module 1184 is mounted adjacent to the TLCL assembly 1108. In the illustrated embodiment, the probe module 1184 has a power source embodied by a battery 1186 which is enclosed in the probe module 1184. The battery 1186 is used to power the TLCL assembly 1108 during use and/or any of the optical components of the imaging assembly 1104. In an embodiment, the battery 1186 is rechargeable and removable via an access 1188. Moreover, the probe module 1184 has a communication module 1190 having an antenna 1192 for receiving instructions wirelessly from the computer 566, for instance. With such a probe module 1184, remote control of the electrodes (conventional or annularly segmented) is allowed. Further, the images which are detected by the imaging assembly 1104 can be wirelessly communicated to the computer 566 using the antenna 1192 and/or stored on a memory 1198 enclosed in the probe module 1184.

In this embodiment, the TLCL assembly 1108 can be any type of TLCL assembly described herein. For instance, the TLCL assembly 1108 can have a pair of TLCLs that can be configured in the polarization independent configuration or in the aberration compensation configuration. Alternatively, the TLCL assembly 1108 can have four TLCLs configured in the polarization independent configuration and in the aberration compensation configuration (e.g., the TLCL assemblies shown in FIGS. 4A-C).

Figure 12:
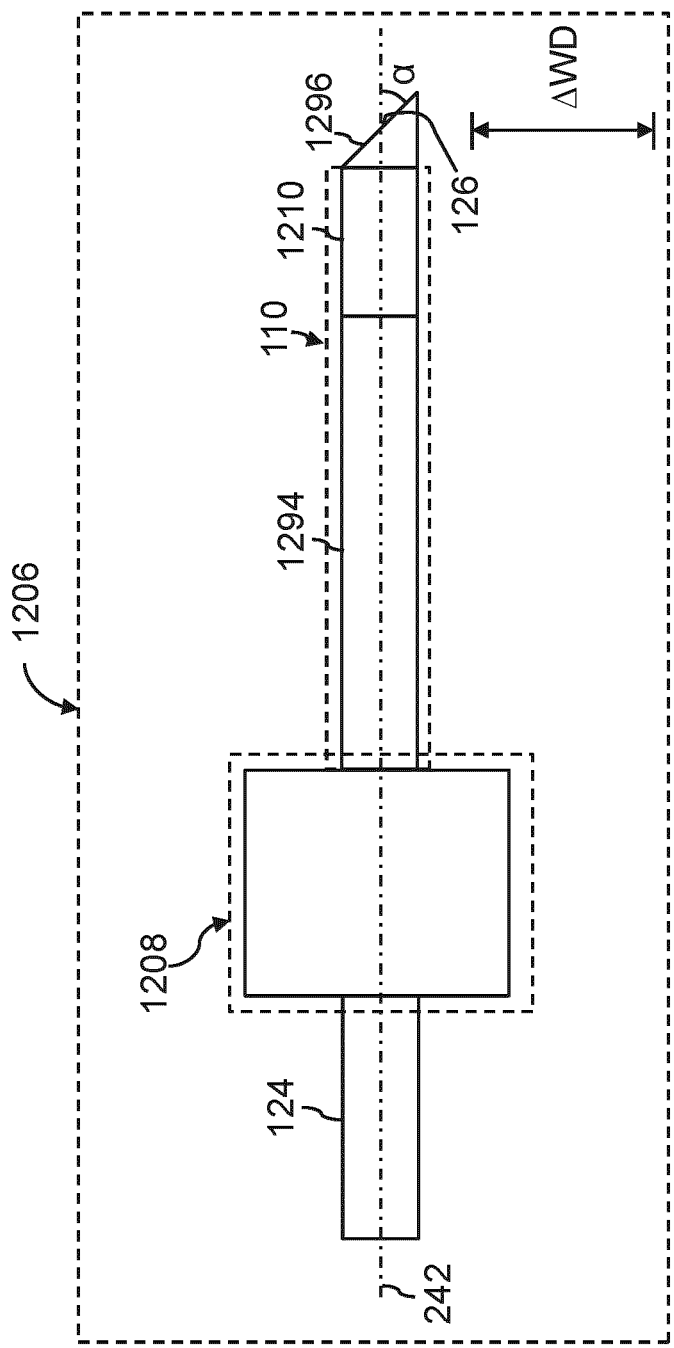
FIG. 12 is a schematic view of an example of a probe with a reflector.

FIG. 12 shows an example of a probe 1206, in accordance with another embodiment. It is understood that the imaging GRIN lens assembly can be a single GRIN lens or a combination of suitable GRIN elements such as waveguide(s) and/or lens(es). In the illustrated embodiment, the imaging GRIN lens assembly 110 comprises a GRIN rod 1294 which propagates the light from the TLCL assembly 1208 to a GRIN focusing lens 1210. The GRIN rod 1294 is optional but useful in situations where the tip of the probe 1206 is to be inserted at a given depth into the specimen.

Still referring to FIG. 12, the probe 1206 has a reflector 1296 positioned at the end of the imaging GRIN lens assembly 110. In this case, the tip 126 is defined by the reflector 1296. The reflector 1296 forms an angle a with respect to an optical axis 242 of the probe 1206 such that the focal point is not only positioned along the optical axis 242 but also along an axis depending on the angle a. As it may be readily understood, rotating the probe 1206 about the optical axis 242, while the probe 1206 is into the specimen, during use, allows imaging a three-dimensional disk of the specimen for each axial position of the probe 1206 into the specimen, for instance. In an embodiment, the reflector 1296 is provided in the form of a piercing member having a sharp edge. With such a piercing member, the probe 1206 can be used to pierce the biological tissue in order to insert the probe 1206 within the biological tissue while minimizing damage caused to the tissue.

Figure 13:
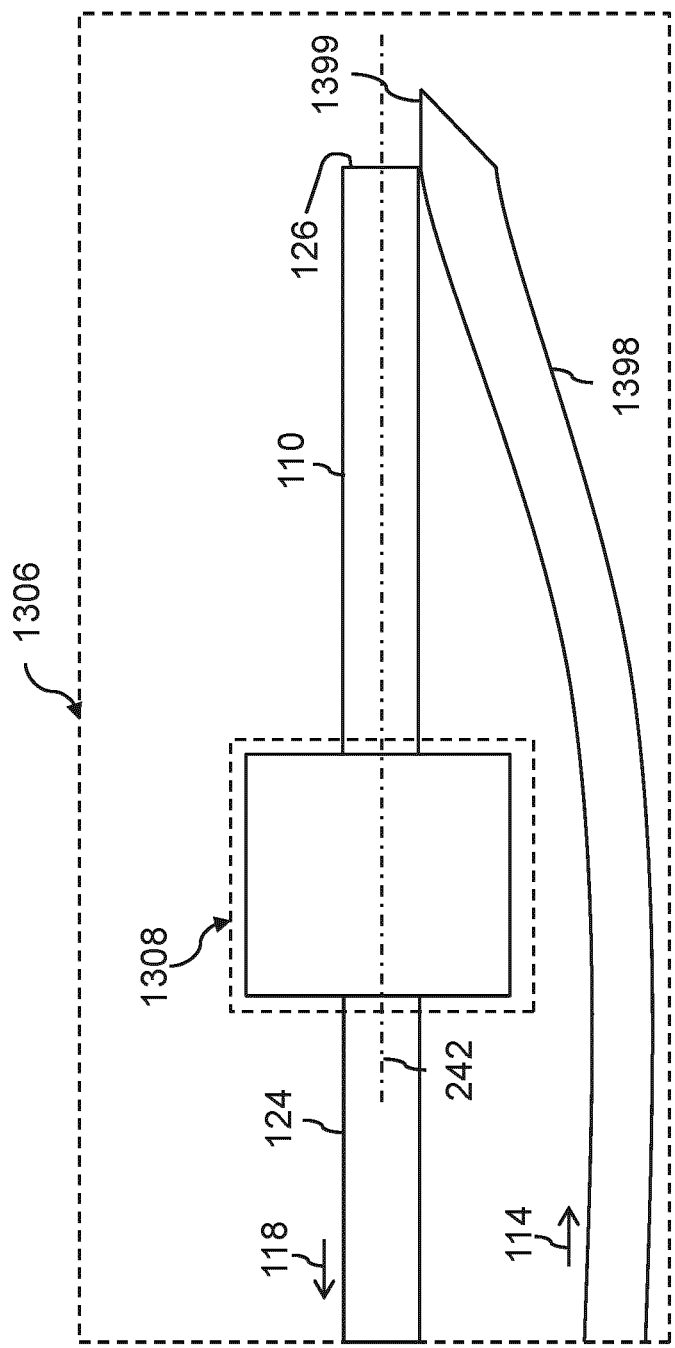
FIG. 13 is a schematic view of an example of a probe with an external illumination fiber, in accordance with an embodiment.

FIG. 13 is a schematic view of a probe 1306, in accordance with an embodiment. As it will be understood by one skilled in the art, the probe 1306 can be configured so that the light from the light source 112 is directed to the specimen without passing through the TLCL assembly 1308 and the imaging GRIN lens 110 by using an external illumination fiber 1398. The illumination light is thus directed along the direction 114, as shown in FIG. 13, while the light received from the specimen 102 is directed along the direction 118, towards the light detector 116. Indeed, the external illumination fiber 1398 can have an end coupled to a light source and another end 1399 provided near the tip 126 of the probe 1306, towards the specimen. The form of the end 1399 is not limited to the angle-polished end shown in FIG. 13, but encompasses other forms deemed suitable by a person skilled in the art.

As it can be understood, the examples described above and illustrated are intended to be exemplary only. The tunable optical device can be used in telecommunication in the form of a tunable collimating lens or a tunable focusing lens or in medical endoscope applications (in vitro or in vivo). Medical applications include, but is not limited to, laparoscopy, arthroscopy, cystoscopy, obstretrics, gynecology, bronchoscopy, laryngoscopy, mediatinoscopy, otoscopy, gastrointestinal, boroscopy and the like. It will be understood that while the embodiments described herein are suitable for imaging specimens, these embodiments can be used, in the same or a modified form, to image other forms of samples, which can consist of inert materials for instance. It will also be understood that in various embodiments, the TLCL/GRIN combination while optically coupled to one another can be separated from one another by distance and/or one or more other optical components. The scope is indicated by the appended claims.

What is claimed is:

1. An imaging system for use in imaging a sample comprising:
    an imaging assembly comprising a light source, an objective and a light detector; and
    a probe optically coupled to the imaging assembly, between the objective and the sample, the probe being configured to, during use, direct light from the light source to a focal point to illuminate the sample, and from the focal point to the light detector, the probe comprising:
    a tunable liquid crystal lens (TLCL) assembly comprising at least one pair of TLCLs, the TLCLs of the pair being superposed to one another,
    a gradient-index (GRIN) lens assembly having a base being optically connected to the TLCL assembly, and
    a tip opposite to the base, the focal point being at a working distance from the tip, the working distance being adjustable relative to the tip by tuning each TLCL of the TLCL assembly during use.

2. The imaging system of claim 1, wherein one TLCL of the pair is rotated by 180 degrees about an optical axis of the probe with respect to the other TLCL of the pair.

3. The imaging system of claim 1, wherein one TLCL of the pair is rotated by 90 degrees about an optical axis of the probe with respect to the other TLCL of the pair.

4. The imaging system of claim 1, wherein the probe further comprises a reflector at an end of the GRIN lens assembly opposite the base, the reflector forming an angle relative to an optical axis of the probe such that the adjustable working distance extends away from the optical axis.

5. The imaging system of claim 1, wherein each TLCL has two electrodes and a LC layer therebetween, the TLCL being tunable by modifying a frequency of a driving signal provided to across the LC layer via the electrodes.

6. The imaging system of claim 1, further comprising a probe module enclosing the imaging assembly, a power source and a communication module such that the imaging system is operable wirelessly as a standalone imaging system.

7. The imaging system of claim 1, further comprising a coupling waveguide optically coupling the imaging assembly to the probe.

8. The imaging system of claim 1, wherein the at least one TLCL of the TLCL assembly has a nominal diameter of at most 1 mm.

9. The imaging system of claim 1, wherein the GRIN lens assembly comprises a GRIN rod optically connected to a focusing GRIN lens.

10. The imaging system of claim 1, wherein the imaging system is configured to illuminate the sample with wavelengths corresponding to excitation wavelengths of different molecules of the sample, the molecules emitting a signal upon excitation such that signal is provided to the optical detector.

11. The imaging system of claim 10, wherein the probe module further encloses a memory for storing images associated with the sample.

12. The imaging system of claim 1, wherein the TLCL assembly comprises two pairs of TLCLs, the TLCLs of the two pairs being superposed to one another, each pair of TLCLs being rotated by 90 degrees from one another about an optical axis of the probe, the two TLCLs of each pair of TLCLs being rotated by 180 degrees from one another about the optical axis of the probe.

13. The imaging system of claim 12, wherein the two TLCLs of the each pair are adjacent from one another.

14. The imaging system of claim 12, wherein the TLCLs of one pair are interspersed with the TLCLs of the other pair.

15. The imaging system of claim 1, wherein the at least one pair of TLCLs of the TLCL assembly have annularly segmented electrodes, the annularly segmented electrodes having a number of electrode segments being independently operable to compensate for aberrations of at least one of the GRIN lens assembly and the sample.

16. The imaging system of claim 15, wherein the annularly segmented electrode has at least four electrode segments.

* * * * *